US008784686B2

(12) United States Patent
Walker

(10) Patent No.: US 8,784,686 B2
(45) Date of Patent: Jul. 22, 2014

(54) LIQUIDS

(75) Inventor: Adam John Walker, Lincolnshire (GB)

(73) Assignee: Innovia Films Limited (GB)

( * ) Notice: Subject to any disclaimer, the term of this patent is extended or adjusted under 35 U.S.C. 154(b) by 69 days.

(21) Appl. No.: 10/599,694

(22) PCT Filed: Apr. 7, 2005

(86) PCT No.: PCT/GB2005/001364
§ 371 (c)(1),
(2), (4) Date: Jan. 19, 2007

(87) PCT Pub. No.: WO2005/097731
PCT Pub. Date: Oct. 20, 2005

(65) Prior Publication Data
US 2007/0185330 A1 Aug. 9, 2007

(30) Foreign Application Priority Data
Apr. 7, 2004 (GB) .................................. 0407908.3

(51) Int. Cl.
B01F 1/00 (2006.01)

(52) U.S. Cl.
USPC .......................... 252/364; 264/37.18; 264/349

(58) Field of Classification Search
USPC ................................ 252/364; 264/37.18, 349
See application file for complete search history.

(56) References Cited

U.S. PATENT DOCUMENTS

| 3,751,561 | A | * | 8/1973 | Wildi et al. .................. 424/48 |
| 4,001,156 | A | * | 1/1977 | Bosso et al. .................. 523/421 |
| 4,189,761 | A | | 2/1980 | Finkelstein et al. |
| 4,191,674 | A | * | 3/1980 | Wismer et al. .............. 525/327.3 |
| 4,219,624 | A | * | 8/1980 | Fuzesi .......................... 521/171 |
| 4,377,654 | A | | 3/1983 | Haas et al. |
| 4,709,083 | A | | 11/1987 | Spielvogel |
| 5,371,166 | A | | 12/1994 | Farkas et al. |
| 5,464,880 | A | | 11/1995 | Weber et al. |
| 6,361,940 | B1 | | 3/2002 | Van Ness et al. |
| 6,472,565 | B1 | | 10/2002 | Bahrmann et al. |
| 6,900,313 | B2 | | 5/2005 | Wasserscheid et al. |
| 2003/0232844 | A1 | * | 12/2003 | Rogier, Jr. et al. ......... 514/260.1 |
| 2008/0191170 | A1 | * | 8/2008 | Walker et al. ................. 252/364 |
| 2008/0221361 | A1 | * | 9/2008 | Walker ......................... 564/508 |
| 2008/0258113 | A1 | * | 10/2008 | Clyburne et al. ............. 252/364 |
| 2011/0257433 | A1 | * | 10/2011 | Walker ......................... 562/579 |

FOREIGN PATENT DOCUMENTS

| DE | 262 042 A1 | 11/1988 |
| DE | 103 06 617 A1 | 8/2004 |
| EP | 0 430 772 A2 | 5/1991 |
| EP | 1 205 555 A1 | 5/2002 |
| EP | 1 736 542 A1 | 12/2006 |
| FR | 2 835 447 A1 | 8/2003 |
| GB | 879259 | 10/1961 |
| GB | 1391922 | 4/1975 |
| GB | 1 509 230 | 5/1978 |
| WO | 01/85129 A2 | 11/2001 |
| WO | WO 0185129 A2 * | 11/2001 |
| WO | 03/060057 A2 | 7/2003 |
| WO | 03/074494 A1 | 9/2003 |
| WO | WO 2004/063383 * | 7/2004 |
| WO | 2004/090066 A1 | 10/2004 |
| WO | 2004/114445 A1 | 12/2004 |

OTHER PUBLICATIONS

Reg. No. 59101-30-3, Nov. 16, 1984.*
Seth et al., "Solvent and Rotational Relaxation of Coumarin 153 in a Protic Ionic Liquid Dimetylethanolammonium Formate", J. Phys. Chem. B, 2008, 112 (9), 2629-2636.*
Walker et al., "Combined biological and chemical catalysis in the preparation of oxycodone", Tetrahedron, 60 (2004), 561-568.*
Walker et al., "Cofactor-dependent enzyme catalysis in functionalized ionic solvents", Chem. Commun., 2004, 2570-2571.*
International Search Report for PCT/GB2005/001364, dated Sep. 22, 2005, 4 pages.
GB Patent Search for GB0506984.4, dated Jul. 27, 2005, 1 page.
Alekseeva, L.V., et al., "On the Synthesis of Folic Acid Fragments", J. Gen. Chem. USSR, 1963, pp. 1649-1650, vol. 33, No. 5.
Anderson, J.L., et al., "Characterizing Ionic Liquids on the Basis of Multiple Solvation Interactions", J. Am. Chem. Soc., 2002, pp. 14247-14254, vol. 124, No. 7.
Armstrong, D.W., et al., "Ionic Liquids as Matrixes for Matrix-Assisted Laser DesorptionIonization Mass Spectrometry", Anal. Chem., 2001, pp. 3679-3686, vol. 73(15).
Bicak, N., "A new ionic liquid: 2-hydroxy ethylammonium formate", J. Mol. Liq., 2005, pp. 15-18, vol. 116.
Database Beilstein, Beilstein Institut zur Forderung der Chemischen Wissenschaften, Database accession No. 3613277 abstract & J. Gen. Chem., USSR 1963, pp. 1649-1650, vol. 33, No. 5.
Database Beilstein, Beilstein Institut zur Forderung der Chemischen Wissenschaften, Database accession No. 3694926 abstract & Biochem. Z, 1953, pp. 485-490, vol. 324.
Database Beilstein, Beilstein Institut zur Forderung der Chemischen Wissenschaften, Database accession No. 5160694 abstract & J. Org. Chem. USSR, 1985, pp. 379-386, vol. 21, No. 2.
CAS Registry 38739-74-1.
CAS Registry 2498-25-1.
CAS Registry 62640-03-3.
CAS Registry 138036-64-3.
CAS Registry 90001-96-0.
Poole, C.F., et al., "Organic Salts, Liquid at Room Temperature, as Mobile Phases in Liquid Chromatography", J. Chrom., 1986, pp. 407-425, vol. 352.
Williams, E., et al., "Pressure Dependence of the Glass Transition Temperature in Ionic Liquids and Solutions. Evidence Against Free Volume Theories.", J. Phy. Chem., 1977, pp. 232-237, vol. 81, No. 3.
CAS Registry No. 137360-57-7.
CAS Registry No. 58937-21-6.
CAS Registry No. 90434-46-1.
Office action from related U.S. Appl. No. 13/170,686, dated Jul. 23, 2012, 6 pgs.

(Continued)

Primary Examiner — Douglas McGinty

(57) ABSTRACT

The present invention relates to ionic liquid comprising an anion and a cation wherein the cation is a primary, secondary or tertiary ammonium ion containing a protonated nitrogen atom.

7 Claims, No Drawings

(56) References Cited

OTHER PUBLICATIONS

CAS Registry No. 38739-74-1; Nov. 16, 1984.
CAS Registry No. 2498-25-1; Nov. 16, 1984.
CAS Registry No. 62640-03-3; Nov. 16, 1984.
CAS Registry No. 138036-64-3; Dec. 21, 1991.
CAS Registry No. 90001-96-0; Nov. 16, 1984.
CAS Registry No. 58937-21-6; Nov. 16, 1984.
CAS Registry No. 90434-46-1; Nov. 16, 1984.
CAS Registry No. 137360-57-7; Nov. 15, 1991.
CAS Registry No. 59101-30-3; Nov. 16, 1984.
Final Office Action from related U.S. Appl. No. 13/170,686 dated Jan. 30, 2013, 8 pages.
Concise Science Dictionary, Oxford University Press, 1984, pp. 242-243.
Non-Final Office Action from related U.S. Appl. No. 13/170,686 dated Jun. 10, 2013, 7 pages.
Final Office Action from related U.S. Appl. No. 13/170,686 dated Jan. 30, 2014, 9 pages.

* cited by examiner

LIQUIDS

The present invention relates to ionic liquids and uses thereof. The invention also provides processes for the manufacture of ionic liquids.

Ionic liquids are compounds which are composed of ions but which have a melting point below ambient temperature. They can be formed by a suitable combination of charge-delocalised, desymmetrised ions. The degree of order of the resulting salt can be reduced and the melting point lowered to a point where the resultant salt is liquid at ambient temperature. The delocalisation of the charge on the ion is also an important factor in determining the melting point of the resulting salt. Ionic liquids possess a number of remarkable properties, including negligible vapour pressure and high solvation capabilities, which have rendered them interesting alternatives to conventional solvents in a variety of applications.

Ionic liquids may be made up of anions and cations or alternatively consist of zwitterions carrying both a positive and a negative charge on the same molecule. Most commonly the ionic liquid will comprise an anion and a cation.

The prior art comprises liquids composed of a quaternary nitrogen- or phosphorus-based cation, for example, based on a nucleus selected from quaternary ammonium cations, pyrrolidinium cations, imidazolium cations, triazolium cations, pyridinium cations, pyridazinium cations, pyrimidinium cations, pyrazinium cations and triazinium cations. These types of ionic liquids tend to be highly viscous, potentially hazardous and strongly absorb UV and visible light. Furthermore, the preparation of these ionic liquids involves a number of chemical and chromatographic steps that makes the process time consuming, expensive and inefficient.

Anderson et al., J. Am. Chem. Soc. 124:14247-14254 (2002) discloses ionic liquids composed of a primary or tertiary ammonium based cation for use in certain chemical applications.

The inventors have provided further ionic liquids.

According to the present invention there is provided an ionic liquid comprising an anion and a cation wherein the cation is a primary, secondary or tertiary ammonium ion containing a charged nitrogen atom.

As used herein a "primary ammonium ion" is an ammonium ion in which the nitrogen has 1 carbon atom attached to it.

As used herein a "secondary ammonium ion" is an ammonium ion in which the nitrogen has 2 carbon atoms attached to it.

As used herein a "tertiary ammonium ion" is an ammonium ion in which the nitrogen has 3 carbon atoms attached to it.

According to a further aspect of the present invention there is provided an ionic liquid comprising an anion and a cation characterised in that the cation is a nitrogen-containing cation of the formula (I)

$$N^+HRR'R'' \qquad (I)$$

in which R is a hydrocarbyl group optionally substituted with by one or more substituents selected from nitrogen-containing functional groups (including nitrile, nitro or amino or another basic nitrogen-containing functional group), thiol, alkythio, sulphonyl, thiocyanate, isothiocyanate, azido, hydrazino, halogen, alkyl optionally interrupted by one or more ether or thioether linkages, alkoxy, alkenyl, hydroxy, carbonyl (including aldehyde or ketone), carboxyl, boronate, silyl and substituted amino (e.g. mono- or di-alkylamino or alkyamido); and R' and R", which may be the same or different, each represent H or R;

or any two or three of R, R' and R" may be joined together with the N to form a cyclic group.

The term "ionic liquid" herein includes, but is not limited to, compounds consisting of ions and liquid at temperatures at which the compound is stable and the ionic liquids may have a melting point below 100° C., for example, below 25° C. and optionally below 20° C. The boiling point of the ionic liquid may be at least 200° C. It may be above 500° C. or even above 1000° C.

The ionic liquids of the invention may consist entirely of ions, which are liquid at the previously above defined temperatures in the dry state. Such ionic liquids will generally contain less than 1% water, preferably less than 1000 ppm water and more preferably still less than 100 ppm water by mass.

In a preferred aspect of the invention, ionic liquids are defined as compounds consisting of a cation and an anion and having a water content of less than 100 parts per million. Preferably still, the ionic liquids have a melting point of 30° C. or below, and a viscosity of less than 500 centipoise.

For the purposes of this invention hydrocarbyl includes, but is not limited to, alkyl, alkenyl, alkynyl, cyclohydrocarbyl, for example cycloalkyl, cycloalkenyl and moieties containing a combination thereof.

As used herein "alkyl" relates to both straight chain and branched alkyl radicals, for example, of 1 to 12 carbon atoms, e.g. 1, 2, 3, 4, 5, 6, 7, 8 carbon atoms including but not limited to methyl, ethyl, n-propyl, isopropyl, n-butyl, sec-butyl, isobutyl, tert-butyl, n-pentyl, n-hexyl, n-heptyl, n-octyl. The term alkyl also encompasses cycloalkyl radicals including but not limited to cyclopropyl, cyclobutyl, cyclopentyl or cyclohexyl.

The alkyl group may be substituted with one or more halogen atoms. In one class of compounds the halogen is fluorine, in another it is chlorine, in a third it is a combination of fluorine and chlorine.

"Alkoxy" relates to both straight chain and branched alkyl radicals, for example, of 1 to 12 carbon atoms, e.g. 1, 2, 3, 4, 5, 6, 7, 8 carbon atoms containing one or more oxygen atoms or hydroxyl.

The term "alkenyl" means a straight or branched alkenyl radical of, for example, 2 to 12 carbon atoms, such as 2, 3, 4, 5 or 6 carbon atoms, and containing one or more carbon-carbon double bonds and includes but is not limited to ethylene, n-propyl-1-ene, n-propyl-2-ene, isopropylene etc.

"Alkynyl" relates to a straight or branched alkynyl radical of, for example, 2 to 12 carbon atoms, such as 2, 3, 4, 5 or 6 carbon atoms, and containing one or more triple bonds.

"Cyclohydrocarbyl" relates to a saturated, partly unsaturated or unsaturated 3-10, for example, 5, 6, 7, 8, 9 or 10, membered hydrocarbon ring, including cycloalkyl or aryl.

"Aryl" means an aromatic, for example, 6-10 membered hydrocarbon containing one, e.g. 6C-10C, ring which is optionally fused to one or more saturated or unsaturated rings, including phenyl or phenyl substituted by an alkyl or alkoxy group in which alkyl and alkoxy are as described herein.

"Heteroaryl" means an aromatic, for example, 5-10 membered aromatic ring containing one or more heteroatoms selected from N, O or S, and containing one ring which is optionally fused to one or more saturated or unsaturated rings.

"Heterocyclyl" means, for example, a 3-10 membered ring system containing one or more heteroatoms selected from N, O or S and includes heteroaryl. The heterocyclyl system may contain one ring or may be fused to one or more saturated or unsaturated rings; the heterocyclyl may be fully saturated, partially saturated or unsaturated.

"Cyclic group" means a ring or ring system, which may be unsaturated or partially unsaturated but is usually saturated, typically containing 5 to 13 ring-forming atoms, for example a 5- or 6-membered ring. Examples include cyclohydrocarbyl or heterocyclyl.

Examples of cyclohydrocarbyl or heterocyclyl groups include but are not limited to cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isooxazole, isothiazole, morpholine, napthyridine, oxazole, oxadiazole, oxathiazole, oxathiazolidine, oxazine, oxadiazine, phenazine, phenothiazine, phenoxazne, phthalazine, piperazine, piperidine, pteridine, purine, putrescine, pyran, pyrazine, pyrazole, pyrazoline, pyrazolidine, pyridazine, pyridine, pyrimidine, pyrrolidine, pyrrole, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, trithiane, tropine.

Halogen means F, Cl, Br, or I.

In one class of compounds R' and R" are H. Compounds such as these having 1 R group and 3 hydrogens are referred to herein as primary ammonium ions.

The invention covers compounds of formula (I) having 2 R groups and 2 hydrogens and which are referred to herein as secondary ammonium ions respectively. The invention further covers compounds having 3 R groups and 1 hydrogen and which are referred to herein as tertiary ammonium ions.

Included is a class of compounds in which R' and R" are different and have the same meaning as R.

In a preferred aspect of the invention there is provided an ionic liquid consisting of an anion and a cation as defined in the first aspect of the invention.

In a preferred aspect of the invention the cyclic group is a cyclohydrocarbyl or hetereocyclyl group, for example cyclohexylammonium.

In one class of compounds there are excluded cations wherein any two or three of R, R', R" may be joined together with the N to form an aryl or heteroaryl group. Specifically excluded are pyridinium, pyrrolidinium and imidazolium cations. In one class of compounds where R is unsubstituted, there are excluded cations where R, R'and R" are the same and are ethyl or butyl.

In one class of compounds wherein R, R' and/or R" is an unsubstituted hydrocarbyl group, the invention may include the following provisos:

Where R is ethyl, the invention may include the proviso that R' and/or R" are not H.

Where R' and R" are both $CH_3$, the invention may include the proviso that R is not H.

Where one or R' and R" is H and the other is $CH_3$, the invention may include the proviso that R is not $CH_3$.

The invention may include the proviso that the ionic liquid is not any of the following:
Ethylammonium nitrate
Tributylammonium-acetate
Tributylammonium α-cyano-4-hydroxycinnamate
Tributylammonium sinapate
Dimethylammonium pyridine-2-carboxylate
Tributylammonium pyridine-2-carboxylate
Tributylammonium 3-hydroxypyridine-2-carboxylate
Triethylammonium pyridine-2-carboxylate In addition to demonstrating high solvation capability, the ionic liquids of the present invention have a low viscosity, are non-toxic and are colourless. These features make the ionic liquids of the present invention useful in a variety of applications.

Preferably, R is substituted with a moiety selected from the group consisting of alkenyl, hydroxyl, amino, thio, carbonyl and carboxyl groups. More preferably, R is substituted with a hydroxyl or amino group.

In one class of compounds, where R is substituted with a hydroxyl group, the invention may include the proviso that the ionic liquid is not diethanolammonium chloride.

If more than one substituent group (for example, selected from the group consisting of alkenyl, hydroxyl, amino, thiol, carbonyl and carboxyl groups) is present then more than one substituent group may be present on a single cation.

In one class of compounds, R is a hydroxyalkyl group having 1, 2, 3, 4, 5 or 6 C atoms. The hydroxyalkyl group may have a hydroxyl moiety on its free, terminal carbon. R may be a polyol having 2 to 6 C atoms, for example, a di-alkanol, tri-alkanol or tetra-alkanol group.

Preferably, the cation is an ethanolammonium, N-(alkoxyethyl)ammonium, N-methylethanolammonium, N,N-dimethylethanolammonium, diethanolammonium, N-alkyldiethanolammonium (e.g butyldiethanolammonium), N,N-di(alkoxyalkyl)ammonium (e.g di(methoxyethyl)ammonium) or triethanolammonium ion.

More preferably the cation is a methylethanolammonium, N,N dimethylethanolammonium, N, N-di(methoxyethyl)ammonium) or butyldiethanolammonium ion.

In another class of compounds, R is an aminoalkyl group having 2 to 8 C atoms, for example, 2, 3, 4, 5, 6, 7 or 8 C atoms. The aminoalkyl may be a di or tri-aminoalkyl group.

In some compounds, R is putrescine, piperidine, or tropine.

Preferred cations include an ethanolammonium, diethanolammonium, N-butyldiethanolammonium, N-methylethanolammonium, di(methoxyethyl)ammonium, N,N-dimethylethanolammonium, putrescinium, 1-(3-hydroxypropyl) putrescinium, or N-(3-hydroxypropyl)-N-methylcyclohexylammonium ion. Preferably still, cations include N-butyldiethanolammonium, N-methylethanolammonium, di(methoxyethyl)ammonium, N,N-dimethylethanolammonium, putrescinium, 1-(3-hydroxypropyl)putrescinium, or N-(3-hydroxypropyl)-N-methylcyclohexylammonium ion.

Any cation included in the above list may be combined with any disclosed anion.

The identity of the anions in the ionic liquids of the invention is not critical. The only theoretical constraint upon the choice of the anion is its ionic weight in order to keep the melting point of the ionic liquid below the desired temperature.

Preferably the anion is selected from halogenated inorganic anions, nitrates, sulphates, phosphates, carbonates, sulphonates and carboxylates. The sulphonates and carboxylates may be alkylsulphonates and alkylcarboxylates, in which the alkyl group is a moiety, for example having 1 to 20 C atoms, selected alkyl and alkyl substituted at any position with alkenyl, alkoxy, alkeneoxy, aryl, arylalkyl, aryloxy, amino, aminoalkyl, thio, thioalkyl, hydroxyl, hydroxyalkyl, carbonyl, oxoalkyl, carboxyl, carboxyalkyl or halide function, including all salts, ethers, esters, pentavalent nitrogen or phosphorus derivatives or stereoisomers thereof. For example, the anion may be selected from bis(trifluoromethylsulphonyl) imide, carbonate, hydrogen carbonate, sulphate, hydrogen sulphate, silicate, phosphate, hydrogen phosphate, dihydrogen phosphate, metaphosphate, methanesulphonate, trifluoromethanesulphonate, ethylenediaminetetraacetate, chloride, bromide, iodide, hexafluorophosphate, tetrafluoroborate, trifluoroacetate, pentafluoropropanoate, heptafluorobutanoate, oxalate, formate, acetate, propanoate, butanoate, pentanoate, hexanoate, heptanoate, octanoate, nonanoate, decanoate, benzoate, benezenedicarboxylate, benzenetricarboxylate, benzenetetracarboxylate, chlorobenzoate, fluorobenzoate, pentachlorobenzoate, pentafluorobenzoate salicylate, glycolate lactate, pantothenate, tartrate, hydrogen tartrate, mandelate, crotonate, malate, pyruvate, succinate, citrate, fumarate, phenylacetate. An especially preferred anion is an organic carboxylate. When the anion is required to include a labile proton then glycolate, tartrate and lactate anions are preferred. These contain both acid and hydroxyl functional groups.

The ionic liquid according to the invention may contain cations which are all the same or which are different. In the same way, the ionic liquids may contain anions which are all the same or which are different. Thus the invention encompasses ionic liquids including a mixture of different cations and/or different anions.

Ionic liquids of the invention may include any of the following:
Ethanolammonium formate
Ethanolammonium acetate
Ethanolammonium propanoate
Ethanolammonium propanedioate
Ethanolammonium butanoate
Ethanolammonium butenoate
Ethanolammonium butanedioate
Ethanolammonium pentanoate
Ethanolammonium pentanedioate
Ethanolammonium pentenoate
Ethanolammonium hexanoate
Ethanolammonium hexanedioate
Ethanolammonium hexenoate
Ethanolammonium heptanoate
Ethanolammonium heptanedioate
Ethanolammonium heptenoate
Ethanolammonium octanoate
Ethanolammonium octanedioate
Ethanolammonium octenoate
Ethanolammonium nonanoate
Ethanolammonium nonanedioate
Ethanolammonium nonenoate
Ethanolammonium decanoate
Ethanolammonium decanedioate
Ethanolammonium decenoate
Ethanolammonium undecanoate
Ethanolammonium undecanedioate
Ethanolammonium undecenoate
Ethanolammonium dodecanoate
Ethanolammonium dodecanedicarboxylate
Ethanolammonium dodecenecarboxylate
Ethanolammonium cyclohexanecarboxylate
Ethanolammonium cyclohexenecarboxylate
Ethanolammonium phenoxide
Ethanolammonium benzoate
Ethanolamnonium benezenedicarboxylate
Ethanolammonium benzenetricarboxylate
Ethanolammonium benzenetetracarboxylate
Ethanolammonium chlorobenzoate
Ethanolammonium fluorobenzoate
Ethanolammonium pentachlorobenzoate
Ethanolammonium pentafluorobenzoate
Ethanolammonium salicylate
Ethanolammonium glycolate
Ethanolammonium lactate
Ethanolammonium pantothenate
Ethanolammonium tartrate
Ethanolammonium hydrogen tartrate
Ethanolammonium mandelate
Ethanolammonium crotonate
Ethanolammonium malate
Ethanolammonium pyruvate
Ethanolammonium succinate
Ethanolammonium citrate
Ethanolammonium fumarate
Ethanolammonium phenylacetate
Ethanolammonium oxalate
Ethanolammonium bis(trifluoromethylsulphonyl)imide
Ethanolammonium carbonate
Ethanolammonium hydrogen carbonate
Ethanolammonium sulphate
Ethanolammonium hydrogen sulphate
Ethanolammonium phosphate
Ethanolammonium hydrogen phosphate
Ethanolammonium dihydrogen phosphate
Ethanolammonium methanesulfonate
Ethanolammonium trifluoromethanesulphonate
Ethanolammonium ethylenediaminetetraacetate
Ethanolammonium hexafluorophosphate
Ethanolammonium tetrafluoroborate
Ethanolammonium trifluoroacetate
Ethanolammonium pentafluoropropanoate
Ethanolammonium heptafluorobutanoate
Ethanolammonium phosphoenolpyruvate
Ethanolammonium nicotinamide adenine dinucleotide phosphate
Ethanolammonium adenosinephosphate
Ethanolammonium adenosine diphosphate
Ethanolammonium adenosine triphosphate
Ethanolammonium oxyniacate
Ethanolammonium nitrate
Ethanolammonium nitrite
Diethanolammonium bromide
Diethanolammonium iodide
Diethanolammonium formate
Diethanolammonium acetate
Diethanolammonium propanoate
Diethanolammonium propanedioate
Diethanolammonium butanoate
Diethanolammonium butenoate
Diethanolammonium butanedioate
Diethanolammonium pentanoate
Diethanolammonium pentanedioate
Diethanolammonium pentenoate
Diethanolammonium hexanoate
Diethanolammonium hexanedioate
Diethanolammonium hexenoate
Diethanolammonium heptanoate
Diethanolammonium heptanedioate
Diethanolammonium heptenoate
Diethanolammonium octanoate
Diethanolammonium octanedioate
Diethanolammonium octenoate
Diethanolammonium nonanoate
Diethanolammonium nonanedioate
Diethanolammonium nonenoate
Diethanolammonium decanoate
Diethanolammonium decanedioate
Diethanolammonium decenoate
Diethanolammonium undecanoate
Diethanolammonium undecanedioate Diethanolammonium undecenoate
Diethanolammonium dodecanoate
Diethanolammonium dodecanedicarboxylate
Diethanolammonium dodecenecarboxylate
Diethanolammonium cyclohexanecarboxylate
Diethanolammonium cyclohexenecarboxylate
Diethanolammonium phenoxide
Diethanolammonium benzoate
Diethanolammonium benezenedicarboxylate
Diethanolammonium benzenetricarboxylate
Diethanolammonium benzenetetracarboxylate
Diethanolammonium chlorobenzoate
Diethanolammonium fluorobenzoate
Diethanolammonium pentachlorobenzoate
Diethanolammonium pentafluorobenzoate
Diethanolammonium salicylate
Diethanolammonium glycolate
Diethanolammonium lactate
Diethanolammonium pantothenate
Diethanolammonium tartrate
Diethanolammonium hydrogen tartrate
Diethanolammonium mandelate
Diethanolammonium crotonate
Diethanolammonium malate
Diethanolammonium pyruvate
Diethanolammonium succinate
Diethanolammonium citrate
Diethanolammonium fumarate
Diethanolammonium phenylacetate
Diethanolammonium oxalate
Diethanolammonium bis(trifluoromethylsulphonyl)imide
Diethanolammonium carbonate
Diethanolammonium hydrogen carbonate
Diethanolammonium phosphate
Diethanolammonium hydrogen phosphate
Diethanolammonium dihydrogen phosphate
Diethanolammonium methanesulphonate
Diethanolammonium trifluoromethanesulphonate
Diethanolammonium ethylenediaminetetraacetate
Diethanolammonium hexafluorophosphate
Diethanolammonium tetrafluoroborate
Diethanolammonium trifluoroacetate
Diethanolammonium pentafluoropropanoate
Diethanolammonium heptafluorobutanoate
Diethanolammonium phosphoenolpyruvate
Diethanolammonium nicotinamide adenine dinucleotide phosphate
Diethanolammonium adenosinephosphate
Diethanolammonium adenosine diphosphate
Diethanolammonium adenosine triphosphate
Diethanolammonium oxyniacate
Diethanolammonium nitrate
Diethanolammonium nitrite
N-Butyldiethanolammonium chloride
N-Butyldiethanolammonium bromide
N-Butyldiethanolammonium iodide
N-Butyldiethanolammonium formate
N-Butyldiethanolammonium acetate
N-Butyldiethanolammonium propanoate
N-Butyldiethanolammonium propanedioate
N-Butyldiethanolammonium butanoate
N-Butyldiethanolammonium butenoate
N-Butyldiethanolammonium butanedioate
N-Butyldiethanolammonium pentanoate
N-Butyldiethanolammonium pentanedioate
N-Butyldiethanolammonium pentenoate
N-Butyldiethanolammonium hexanoate
N-Butyldiethanolammonium hexenoate
N-Butyldiethanolammonium heptanoate
N-Butyldiethanolammonium heptanedioate
N-Butyldiethanolammonium heptenoate
N-Butyldiethanolammonium octanoate
N-Butyldiethanolammonium octanedioate
N-Butyldiethanolammonium octenoate
N-Butyldiethanolammonium nonanoate
N-Butyldiethanolammonium nonanedioate
N-Butyldiethanolammonium nonenoate
N-Butyldiethanolammonium decanoate
N-Butyldiethanolammonium decanedioate
N-Butyldiethanolammonium decenoate
N-Butyldiethanolammonium undecanoate
N-Butyldiethanolammonium undecanedioate
N-Butyldiethanolammonium undecenoate
N-Butyldiethanolammonium dodecanoate
N-Butyldiethanolammonium dodecanedicarboxylate
N-Butyldiethanolammonium dodecenecarboxylate
N-Butyldiethanolammonium cyclohexanecarboxylate
N-Butyldiethanolammonium cyclohexenecarboxylate
N-Butyldiethanolammonium phenoxide
N-Butyldiethanolammonium benzoate
N-Butyldiethanolammonium benezenedicarboxylate
N-Butyldiethanolammonium benzenetricarboxylate
N-Butyldiethanolammonium benzenetetracarboxylate
N-Butyldiethanolammonium chlorobenzoate
N-Butyldiethanolammonium fluorobenzoate
N-Butyldiethanolammonium pentachlorobenzoate
N-Butyldiethanolammonium pentafluorobenzoate
N-Butyldiethanolammonium salicylate
N-Butyldiethanolammonium glycolate
N-Butyldiethanolammonium lactate
N-Butyldiethanolammonium pantothenate
N-Butyldiethanolammonium tartrate
N-Butyldiethanolammonium hydrogen tartrate
N-Butyldiethanolammonium mandelate
N-Butyldiethanolammonium crotonate
N-Butyldiethanolammonium malate
N-Butyldiethanolammonium pyruvate
N-Butyldiethanolammonium succinate
N-Butyldiethanolammonium citrate
N-Butyldiethanolammonium fumarate
N-Butyldiethanolammonium phenylacetate
N-Butyldiethanolammonium oxalate
N-Butyldiethanolammonium bis(trifluoromethylsulphonyl)imide
N-Butyldiethanolammonium carbonate
N-Butyldiethanolammonium hydrogen carbonate
N-Butyldiethanolammonium sulphate
N-Butyldiethanolammonium hydrogen sulphate
N-Butyldiethanolammonium phosphate
N-Butyldiethanolammonium hydrogen phosphate
N-Butyldiethanolammonium dihydrogen phosphate
N-Butyldiethanolammonium methanesulphonate
N-Butyldiethanolammonium trifluoromethanesulphonate
N-Butyldiethanolammonium ethylenediaminetetraacetate
N-Butyldiethanolammonium hexafluorophosphate
N-Butyldiethanolammonium tetrafluoroborate
N-Butyldiethanolammonium trifluoroacetate
N-Butyldiethanolammonium pentafluoropropanoate
N-Butyldiethanolammonium heptafluorobutanoate
N-Butyldiethanolammonium phosphoenolpyruvate
N-Butyldiethanolammonium nicotinamide adenine dinucleotide phosphate
N-Butyldiethanolammonium adenosinephosphate
N-Butyldiethanolammonium adenosine diphosphate N-Butyldiethanolammonium adenosine triphosphate
N-Butyldiethanolammonium oxyniacate
N-Butyldiethanolammonium nitrate
N-Butyldiethanolammonium nitrite
N,N-Dimethylethanolammonium bromide
N,N-Dimethylethanolammonium iodide
N,N-Dimethylethanolammonium formate
N,N-Dimethylethanolammonium acetate
N,N-Dimethylethanolammonium propanoate
N,N-Dimethylethanolammonium propanedioate
N,N-Dimethylethanolammonium butanoate
N,N-Dimethylethanolammonium butenoate
N,N-Dimethylethanolammonium butanedioate
N,N-Dimethylethanolammonium pentanoate
N,N-Dimethylethanolammonium pentanedioate
N,N-Dimethylethanolammonium pentenoate
N,N-Dimethylethanolammonium hexanoate
N,N-Dimethylethanolammonium hexenoate
N,N-Dimethylethanolammonium heptanoate
N,N-Dimethylethanolammonium heptanedioate
N,N-Dimethylethanolammonium heptenoate
N,N-Dimethylethanolammonium octanoate
N,N-Dimethylethanolammonium octanedioate
N,N-Dimethylethanolammonium octenoate
N,N-Dimethylethanolammonium nonanoate
N,N-Dimethylethanolammonium nonanedioate
N,N-Dimethylethanolammonium nonenoate
N,N-Dimethylethanolammonium decanoate
N,N-Dimethylethanolammonium decanedioate
N,N-Dimethylethanolammonium decenoate
N,N-Dimethylethanolammonium undecanoate
N,N-Dimethylethanolammonium undecanedioate
N,N-Dimethylethanolammonium undecenoate
N,N-Dimethylethanolammonium dodecanoate
N,N-Dimethylethanolammonium dodecanedicarboxylate
N,N-Dimethylethanolammonium dodecenecarboxylate
N,N-Dimethylethanolammonium cyclohexanecarboxylate
N,N-Dimethylethanolammonium cyclohexenecarboxylate
N,N-Dimethylethanolammonium phenoxide
N,N-Dimethylethanolammonium benzoate
N,N-Dimethylethanolammonium benezenedicarboxylate
N,N-Dimethylethanolammonium benzenetricarboxylate
N,N-Dimethylethanolammonium benzenetetracarboxylate
N,N-Dimethylethanolammonium chlorobenzoate
N,N-Dimethylethanolammonium fluorobenzoate
N,N-Dimethylethanolammonium pentachlorobenzoate
N,N-Dimethylethanolammonium pentafluorobenzoate
N,N-Dimethylethanolammonium salicylate
N,N-Dimethylethanolammonium glycolate
N,N-Dimethylethanolammonium lactate
N,N-Dimethylethanolammonium pantothenate
N,N-Dimethylethanolammonium tartrate
N,N-Dimethylethanolammonium hydrogen tartrate
N,N-Dimethylethanolammonium mandelate
N,N-Dimethylethanolammonium crotonate
N,N-Dimethylethanolammonium malate
N,N-Dimethylethanolammonium pyruvate
N,N-Dimethylethanolammonium succinate
N,N-Dimethylethanolammonium citrate
N,N-Dimethylethanolammonium fumarate
N,N-Dimethylethanolammonium phenylacetate
N,N-Dimethylethanolammonium oxalate
N,N-Dimethylethanolammonium bis(trifluoromethylsulphonyl)imide
N,N-Dimethylethanolammonium carbonate
N,N-Dimethylethanolammonium hydrogen carbonate
N,N-Dimethylethanolammonium sulphate
N,N-Dimethylethanolammonium hydrogen sulphate
N,N-Dimethylethanolammonium phosphate
N,N-Dimethylethanolammonium hydrogen phosphate
N,N-Dimethylethanolammonium dihydrogen phosphate
N,N-Dimethylethanolammonium methanesulphonate
N,N-Dimethylethanolammonium trifluoromethanesulphonate
N,N-Dimethylethanolammonium ethylenediaminetetraacetate
N,N-Dimethylethanolammonium hexafluorophosphate
N,N-Dimethylethanolammonium tetrafluoroborate
N,N-Dimethylethanolammonium trifluoroacetate
N,N-Dimethylethanolammonium pentafluoropropanoate
N,N-Dimethylethanolammonium heptafluorobutanoate
N,N-Dimethylethanolammonium phosphoenolpyruvate
N,N-Dimethylethanolammonium nicotinamide adenine dinucleotide phosphate
N,N-Dimethylethanolammonium adenosinephosphate
N,N-Dimethylethanolammonium adenosine diphosphate
N,N-Dimethylethanolammonium adenosine triphosphate
N,N-Dimethylethanolammonium oxyniacate
N,N-Dimethylethanolammonium nitrate
N,N-Dimethylethanolammonium nitrite
N-Methylethanolammonium bromide
N-Methylethanolammonium iodide
N-Methylethanolammonium formate
N-Methylethanolammonium acetate
N-Methylethanolammonium propanoate
N-Methylethanolammonium propanedioate
N-Methylethanolammonium butanoate
N-Methylethanolammonium butenoate
N-Methylethanolammonium butanedioate
N-Methylethanolammonium pentanoate
N-Methylethanolammonium pentanedioate
N-Methylethanolammonium pentenoate
N-Methylethanolammonium hexanoate
N-Methylethanolammonium hexenoate
N-Methylethanolammonium heptanoate
N-Methylethanolammonium heptanedioate
N-Methylethanolammonium heptenoate
N-Methylethanolammonium octanoate
N-Methylethanolammonium octanedioate
N-Methylethanolammonium octenoate
N-Methylethanolammonium nonanoate
N-Methylethanolammonium nonanedioate
N-Methylethanolammonium nonenoate
N-Methylethanolammonium decanoate
N-Methylethanolammonium decanedioate
N-Methylethanolammonium decenoate
N-Methylethanolammonium undecanoate
N-Methylethanolammonium undecanedioate
N-Methylethanolammonium undecenoate
N-Methylethanolammonium dodecanoate
N-Methylethanolammonium dodecanedicarboxylate
N-Methylethanolammonium dodecenecarboxylate
N-Methylethanolammonium cyclohexanecarboxylate
N-Methylethanolammonium cyclohexenecarboxylate
N-Methylethanolammonium phenoxide
N-Methylethanolammonium benzoate
N-Methylethanolammonium benezenedicarboxylate
N-Methylethanolammonium benzenetricarboxylate
N-Methylethanolammonium benzenetetracarboxylate
N-Methylethanolammonium chlorobenzoate
N-Methylethanolammonium fluorobenzoate
N-Methylethanolammonium pentachlorobenzoate
N-Methylethanolammonium pentafluorobenzoate
N-Methylethanolammonium salicylate N-Methylethanolammonium glycolate
N-Methylethanolammonium lactate
N-Methylethanolammonium pantothenate
N-Methylethanolammonium tartrate
N-Methylethanolammonium hydrogen tartrate
N-Methylethanolammonium mandelate
N-Methylethanolammonium crotonate
N-Methylethanolammonium malate
N-Methylethanolammonium pyruvate
N-Methylethanolammonium succinate
N-Methylethanolammonium citrate
N-Methylethanolammonium fumarate
N-Methylethanolammonium phenylacetate
N-Methylethanolammonium oxalate
N-Methylethanolammonium bis(trifluoromethylsulphonyl) imide
N-Methylethanolammonium carbonate
N-Methylethanolammonium hydrogen carbonate
N-Methylethanolammonium sulphate
N-Methylethanolammonium hydrogen sulphate
N-Methylethanolammonium phosphate
N-Methylethanolammonium hydrogen phosphate
N-Methylethanolammonium dihydrogen phosphate
N-Methylethanolammonium methanesulphonate
N-Methylethanolammonium trifluoromethanesulphonate
N-Methylethanolammonium ethylenediaminetetraacetate
N-Methylethanolammonium hexafluorophosphate
N-Methylethanolammonium tetrafluoroborate
N-Methylethanolammonium trifluoroacetate
N-Methylethanolammonium pentafluoropropanoate
N-Methylethanolammonium heptafluorobutanoate
N-Methylethanolammonium phosphoenolpyruvate
N-Methylethanolammonium nicotinamide adenine dinucleotide phosphate
N-Methylethanolammonium adenosinephosphate
N-Methylethanolammonium adenosine diphosphate
N-Methylethanolammonium adenosine triphosphate
N-Methylethanolammonium oxyniacate
N-Methylethanolammonium nitrate
N-Methylethanolammonium nitrite
N,N-Di(methoxyethyl)ammonium chloride
N,N-Di(methoxyethyl)ammonium bromide
N,N-Di(methoxyethyl)ammonium iodide
N,N-Di(methoxyethyl)ammonium formate
N,N-Di(methoxyethyl)ammonium acetate
N,N-Di(methoxyethyl)ammonium propanoate
N,N-Di(methoxyethyl)ammonium propanedioate
N,N-Di(methoxyethyl)ammonium butanoate
N,N-Di(methoxyethyl)ammonium butenoate
N,N-Di(methoxyethyl)ammonium butanedioate
N,N-Di(methoxyethyl)ammonium pentanoate
N,N-Di(methoxyethyl)ammonium pentanedioate
N,N-Di(methoxyethyl)ammonium pentenoate
N,N-Di(methoxyethyl)ammonium hexanoate
N,N-Di(methoxyethyl)ammonium hexenoate
N,N-Di(methoxyethyl)ammonium heptanoate
N,N-Di(methoxyethyl)ammonium heptanedioate
N,N-Di(methoxyethyl)ammonium heptenoate
N,N-Di(methoxyethyl)ammonium octanoate
N,N-Di(methoxyethyl)ammonium octanedioate
N,N-Di(methoxyethyl)ammonium octenoate
N,N-Di(methoxyethyl)ammonium nonanoate
N,N-Di(methoxyethyl)ammonium nonanedioate
N,N-Di(methoxyethyl)ammonium nonenoate
N,N-Di(methoxyethyl)ammonium decanoate
N,N-Di(methoxyethyl)ammonium decanedioate
N,N-Di(methoxyethyl)ammonium decenoate
N,N-Di(methoxyethyl)ammonium undecanoate
N,N-Di(methoxyethyl)ammonium undecanedioate
N,N-Di(methoxyethyl)ammonium undecenoate
N,N-Di(methoxyethyl)ammonium dodecanoate
N,N-Di(methoxyethyl)ammonium dodecanedicarboxylate
N,N-Di(methoxyethyl)ammonium dodecenecarboxylate
N,N-Di(methoxyethyl)ammonium cyclohexanecarboxylate
N,N-Di(methoxyethyl)ammonium cyclohexenecarboxylate
N,N-Di(methoxyethyl)ammonium phenoxide
N,N-Di(methoxyethyl)ammonium benzoate
N,N-Di(methoxyethyl)ammonium benezenedicarboxylate
N,N-Di(methoxyethyl)ammonium benzenetricarboxylate
N,N-Di(methoxyethyl)ammonium benzenetetracarboxylate
N,N-Di(methoxyethyl)ammonium chlorobenzoate
N,N-Di(methoxyethyl)ammonium fluorobenzoate
N,N-Di(methoxyethyl)ammonium pentachlorobenzoate
N,N-Di(methoxyethyl)ammonium pentafluorobenzoate
N,N-Di(methoxyethyl)ammonium salicylate
N,N-Di(methoxyethyl)ammonium glycolate
N,N-Di(methoxyethyl)ammonium lactate
N,N-Di(methoxyethyl)ammonium pantothenate
N,N-Di(methoxyethyl)ammonium tartrate
N,N-Di(methoxyethyl)ammonium hydrogen tartrate
N,N-Di(methoxyethyl)ammonium mandelate
N,N-Di(methoxyethyl)ammonium crotonate
N,N-Di(methoxyethyl)ammonium malate
N,N-Di(methoxyethyl)ammonium pyruvate
N,N-Di(methoxyethyl)ammonium succinate
N,N-Di(methoxyethyl)ammonium citrate
N,N-Di(methoxyethyl)ammonium fumarate
N,N-Di(methoxyethyl)ammonium phenylacetate
N,N-Di(methoxyethyl)ammonium oxalate
N,N-Di(methoxyethyl)ammonium bis(trifluoromethylsulphonyl)imide
N,N-Di(methoxyethyl)ammonium carbonate
N,N-Di(methoxyethyl)ammonium hydrogen carbonate
N,N-Di(methoxyethyl)ammonium sulphate
N,N-Di(methoxyethyl)ammonium hydrogen sulphate
N,N-Di(methoxyethyl)ammonium phosphate
N,N-Di(methoxyethyl)ammonium hydrogen phosphate
N,N-Di(methoxyethyl)ammonium dihydrogen phosphate
N,N-Di(methoxyethyl)ammonium methanesulphonate
N,N-Di(methoxyethyl)ammonium trifluoromethanesulphonate
N,N-Di(methoxyethyl)ammonium ethylenediaminetetraacetate
N,N-Di(methoxyethyl)ammonium hexafluorophosphate
N,N-Di(methoxyethyl)ammonium tetrafluoroborate
N,N-Di(methoxyethyl)ammonium trifluoroacetate
N,N-Di(methoxyethyl)ammonium pentafluoropropanoate
N,N-Di(methoxyethyl)ammonium heptafluorobutanoate
N,N-Di(methoxyethyl)ammonium phosphoenolpyruvate
N,N-Di(methoxyethyl)ammonium nicotinamide adenine dinucleotide phosphate
N,N-Di(methoxyethyl)ammonium adenosinephosphate
N,N-Di(methoxyethyl)ammonium adenosine diphosphate
N,N-Di(methoxyethyl)ammonium adenosine triphosphate
N,N-Di(methoxyethyl)ammonium oxyniacate
N,N-Di(methoxyethyl)ammonium nitrate
N,N-Di(methoxyethyl)ammonium nitrite
1-(3-Hydroxypropyl)putrescinium chloride
1-(3-Hydroxypropyl)putrescinium bromide
1-(3-Hydroxypropyl)putrescinium iodide
1-(3-Hydroxypropyl)putrescinium formate
1-(3-Hydroxypropyl)putrescinium acetate
1-(3-Hydroxypropyl)putrescinium propanoate
1-(3-Hydroxypropyl)putrescinium propanedioate 1-(3-Hydroxypropyl)putrescinium butanoate
1-(3-Hydroxypropyl)putrescinium butenoate
1-(3-Hydroxypropyl)putrescinium butanedioate
1-(3-Hydroxypropyl)putrescinium pentanoate
1-(3-Hydroxypropyl)putrescinium pentanedioate
1-(3-Hydroxypropyl)putrescinium pentenoate
1-(3-Hydroxypropyl)putrescinium hexanoate
1-(3-Hydroxypropyl)putrescinium hexenoate
1-(3-Hydroxypropyl)putrescinium heptanoate
1-(3-Hydroxypropyl)putrescinium heptanedioate
1-(3-Hydroxypropyl)putrescinium heptenoate
1-(3-Hydroxypropyl)putrescinium octanoate
1-(3-Hydroxypropyl)putrescinium octanedioate
1-(3-Hydroxypropyl)putrescinium octenoate
1-(3-Hydroxypropyl)putrescinium nonanoate
1-(3-Hydroxypropyl)putrescinium nonanedioate
1-(3-Hydroxypropyl)putrescinium nonenoate
1-(3-Hydroxypropyl)putrescinium decanoate
1-(3-Hydroxypropyl)putrescinium decanedioate
1-(3-Hydroxypropyl)putrescinium decenoate
1-(3-Hydroxypropyl)putrescinium undecanoate
1-(3-Hydroxypropyl)putrescinium undecanedioate
1-(3-Hydroxypropyl)putrescinium undecenoate
1-(3-Hydroxypropyl)putrescinium dodecanoate
1-(3-Hydroxypropyl)putrescinium dodecanedicarboxylate
1-(3-Hydroxypropyl)putrescinium dodecenecarboxylate
1-(3-Hydroxypropyl)putrescinium cyclohexanecarboxylate
1-(3-Hydroxypropyl)putrescinium cyclohexenecarboxylate
1-(3-Hydroxypropyl)putrescinium phenoxide
1-(3-Hydroxypropyl)putrescinium benzoate
1-(3-Hydroxypropyl)putrescinium benezenedicarboxylate
1-(3-Hydroxypropyl)putrescinium benzenetricarboxylate
1-(3-Hydroxypropyl)putrescinium benzenetetracarboxylate
1-(3-Hydroxypropyl)putrescinium chlorobenzoate
1-(3-Hydroxypropyl)putrescinium fluorobenzoate
1-(3-Hydroxypropyl)putrescinium pentachlorobenzoate
1-(3-Hydroxypropyl)putrescinium pentafluorobenzoate
1-(3-Hydroxypropyl)putrescinium salicylate
1-(3-Hydroxypropyl)putrescinium glycolate
1-(3-Hydroxypropyl)putrescinium lactate
1-(3-Hydroxypropyl)putrescinium pantothenate
1-(3-Hydroxypropyl)putrescinium tartrate
1-(3-Hydroxypropyl)putrescinium hydrogen tartrate
1-(3-Hydroxypropyl)putrescinium mandelate
1-(3-Hydroxypropyl)putrescinium crotonate
1-(3-Hydroxypropyl)putrescinium malate
1-(3-Hydroxypropyl)putrescinium pyruvate
1-(3-Hydroxypropyl)putrescinium succinate
1-(3-Hydroxypropyl)putrescinium citrate
1-(3-Hydroxypropyl)putrescinium fumarate
1-(3-Hydroxypropyl)putrescinium phenylacetate
1-(3-Hydroxypropyl)putrescinium oxalate
1-(3-Hydroxypropyl)putrescinium bis(trifluoromethylsulphonyl)imide
1-(3-Hydroxypropyl)putrescinium methanesulphonate
1-(3-Hydroxypropyl)putrescinium trifluoromethanesulphonate
1-(3-Hydroxypropyl)putrescinium hexafluorophosphate
1-(3-Hydroxypropyl)putrescinium tetrafluoroborate
1-(3-Hydroxypropyl)putrescinium trifluoroacetate
1-(3-Hydroxypropyl)putrescinium pentafluoropropanoate
1-(3-Hydroxypropyl)putrescinium heptafluorobutanoate
1-(3-Hydroxypropyl)putrescinium phosphoenolpyruvate
1-(3-Hydroxypropyl)putrescinium nicotinamide adenine dinucleotide phosphate
1-(3-Hydroxypropyl)putrescinium adenosinephosphate
1-(3-Hydroxypropyl)putrescinium adenosine diphosphate
1-(3-Hydroxypropyl)putrescinium adenosine triphosphate
1-(3-Hydroxypropyl)putrescinium carbonate
1-(3-Hydroxypropyl)putrescinium hydrogen carbonate
1-(3-Hydroxypropyl)putrescinium sulphate
1-(3-Hydroxypropyl)putrescinium hydrogen sulphate
1-(3-Hydroxypropyl)putrescinium phosphate
1-(3-Hydroxypropyl)putrescinium hydrogen phosphate
1-(3-Hydroxypropyl)putrescinium dihydrogen phosphate
1-(3-Hydroxypropyl)putrescinium nitrate
1-(3-Hydroxypropyl)putrescinium nitrite In one class of compounds, the invention includes the proviso that the ionic liquid is not ethylammonium nitrate or diethanolammonium chloride. In a further class of compounds, the invention includes the proviso that the ionic liquid is not a N-protonated pyridimium or pyrrolidinium salt.

According to a further aspect, the present invention provides a process for the preparation of an ionic liquid according to the invention, the process comprising the steps of:
i.) providing an organic primary, secondary or tertiary amine; and
ii.) neutralising the compound in (i) with an acid.

The process according to the invention may comprise the steps of:
i.) providing a nitrogen-containing compound of the formula (II)

$$NRR'R''\qquad(II)$$

in which R, R' and R'' have the meaning defined herein; and
ii.) neutralising the compound in (i) with an acid.

The process of the present invention provides an economical route to the manufacture of ionic liquids since the process involves only a single step and uses starting materials that are generally readily available.

During the process of the invention, the nitrogen atom of the primary, secondary or tertiary amine is protonated to provide a protonated ammonium ion.

Preferably, the acid includes an anion as defined herein.

Preferably the acid anion comprises a halogenated inorganic anion, nitrate, sulphate, carbonate, sulphonate or carboxylate.

The invention also encompasses compounds of formula (II) and their use in the preparation of one or more ionic liquids.

The invention further provides the use of a cation as defined in the ionic liquids of the present invention in a solvent for enzyme-catalysed reactions. Further provided is the use of an ionic liquid according to the present invention as a solvent for enzyme-catalysed reactions.

The use of ionic liquids in certain biological and/or chemical reactions has several advantages over traditional aqueous solutions. Ionic liquids have an ability to dissolve a wide range of inorganic, organic, polymeric and biological materials, often to a very high concentration. They have a wide liquid range, allowing both high and low temperature processes to be carried out in the same solvent. They do not elicit solvolysis phenomena and most stabilise short-lived reactive intermediates. There are no pH effects in the solvents and there is practically zero vapour pressure over much of the liquid range. Ionic liquids also exhibit excellent electrical and thermal conductivity whilst being non-flammable, recyclable and generally of low toxicity.

The invention further provides the use of an ionic liquid, or of a cation as defined in an ionic liquid, according to the present invention in a solvent for organic synthesis, matrixes in matrix-assisted laser desorption/ionisation (MALDI) mass spectrometry, solvent extraction (e.g to remove desired components from an immiscible liquid or solid) or gas chromatography, catalysis, liquefaction, nuclear fuel reprocessing, fuel cells, electrochemical applications, pervaporation, drug delivery, lubrication, hydraulic fluids, adhesives, sensors, biocides and chromatographic media.

Further provided is a method for carrying out an enzyme-catalysed reaction comprising
i.) providing a liquid reaction medium which comprises an ionic liquid according to the present invention;
ii.) providing in the liquid reaction medium an enzyme and a substrate for the enzyme; and
iii.) allowing reaction of the substrate to occur.

Further provided is a method for the synthesis of one or more organic compounds, the method comprising carrying out an organic synthesis reaction in an ionic liquid according to the present invention.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention will now be described by way of the following, non-limiting examples:

MATERIALS AND METHODS

Preparation of Ammonium-based Ionic Liquids Bearing One or More Ammoniacal Protons The requisite stoichiometric equivalents of the parent amine and complementary acid were dissolved independently in water, methanol or ethanol to give solutions of equal concentrations. Equal volumes of these two solutions were mixed together in a flask, with stirring and cooling, at a rate sufficiently slow as to prevent the temperature of the reaction from exceeding 60° C. When neutralization was complete, the excess solvent was removed in vacuo, at temperatures not exceeding 60° C. The product was then freeze-dried, analysed and stored in a desiccated condition.

Preparation of N,N-dimethylethanolammonium glycolate

Alcoholic solutions of N,N-dimethyethanolamine (100.00 mL, 2.000M concentration) and glycolic acid (100.00 mL, 2.000M concentration) were gradually mixed together in a 500 mL round-bottomed flask, with external cooling and stirring. After completion of the neutralisation reaction, the cold alcoholic solution was filtered, transferred to a clean flask and the solvent was removed on a rotary evaporator. The reaction product was frozen in liquid nitrogen and lyophilised in vacuo, being gradually permitted to rise to room temperature, to yield 32.85 g (99%) of a pale yellow liquid, water content <100 ppm by Karl Fischer titration, purity >99.9% by ion chromatography. The product was analysed by elemental analysis and by infra-red, ultra-violet/visible and nuclear magnetic resonance spectroscopy and was stored over anhydrous calcium chloride in a vacuum desiccator.

FT-IR (cm$^{-1}$): 1591, 1076, 1358, 687, 993, 1468, 909, 1255, 881, 1154, 1171, 3240, 2870, 2484, 1745

UV/vis $\lambda_{max}$ (nm): 234
$E^N_T$ (Reichardt): 0.912
Density (g cm$^{-3}$): 1.146

Preparation of N-butyldiethanolammonium bis(trifluoromethylsulphonyl)imide

To an alcoholic solution of N-butyldiethanolamine (100.00 mL, 2.000M concentration) in a 500 mL round-bottomed flask was gradually added 56.232 g bis(trifluoromethylsulphonyl)imide, with vigorous stirring and external cooling, over a period of 30 minutes. After completion of the reaction, the solution was filtered and the solvent was removed in vacuo. The product was dried as above to yield 87.2 g (98%) of a pale yellow liquid, water content <100 ppm by Karl Fischer titration, purity >98% by ion chromatography. The product was analysed and stored as previously described.

FT-IR (cm$^{-1}$): 1051, 1132, 1181, 1347, 741, 791, 764, 880, 960, 1461, 2967, 3523, 2941, 2880, 3138, 1632

UV/vis $\lambda_{max}$ (nm): 304
$E^N_T$ (Reichardt): 0.994
Density (g cm$^{-3}$): 1.343

Applications

Enzyme-catalysed Reaction in N,N-dimethylethanolammonium glycolate

Alcohol dehydrogenase: Methanol (50 µL) was dissolved in the ionic liquid (6 mL) with a net water content of <100 ppm by Karl Fischer titration. Nicotinamide adenine dinucleotide (100 mg) was added along with lyophilised *Saccharomyces cerevisiae* alcohol dehydrogenase (1 mg). The reaction vessel was sealed and incubated at 30° C. for 24 hours, with vigorous shaking being maintained throughout. Samples (1 mL) were extracted at time points of 0, 2, 4, 8, 12 and 24 hours and were analysed by means of the chromotropic acid assay. The absorbance of the analyte samples at 560 nm was measured against enzyme-free standards and correlated with the concentration of formaldehyde by comparison with a standard curve. The accumulation of formaldehyde was observed up to an equilibrium concentration of 20+/−2 mM.

Biodegradation of N,N-dimethylethanolammonium glycolate

N,N-Dimethylethanolammonium glycolate (5 mM) was used as sole nitrogen and carbon source for the selective enrichment of a mixed community of soil micro-organisms collected from waste ground. Individual organisms were isolated from the mixed culture and were screened for their capability to metabolise the ionic liquid at varying concentrations in aqueous phosphate buffer. Experiments were performed in Erlenmeyer flasks at 30° C., with shaking at 110 rpm. Degradation was monitored using ion chromatography. 5 mM Ionic liquid was readily degraded (>98% removal) within 48 hours, the final nitrogenous metabolite being ammonia.

The invention claimed is:

1. A process for dissolving a polymeric material, the process comprising contacting the polymeric material with an ionic liquid,
the ionic liquid comprising an anion and a cation wherein the cation is a tertiary ammonium ion of the formula (I)

   (I)

wherein:
R is an alkyl group substituted with one or more hydroxy groups;
R' and R" are independently alkyl or substituted alkyl groups optionally substituted with one or more substituents selected from the group consisting of a nitrogen-containing functional group, an alkoxy group, and a hydroxy group; the nitrogen-containing functional group selected from the group consisting of nitrile, nitro, and amino; the substituted alkyl optionally comprising one or more ether linkages; and the anion is selected from the group consisting of a nitrate, sulphate, phosphate, carbonate, sulphonate, and carboxylate.

2. The process of claim 1, wherein the ionic liquid has a melting point below 25° C., a viscosity of less than 500 centipoise, and contains less than 1% water.

3. The process of claim 1, wherein R of the ionic liquid is a hydroxyalkyl having 1, 2, 3, 4, 5 or 6 C atoms.

4. The process of claim 3, wherein the hydroxyalkyl has a hydroxyl moiety on its free, terminal carbon.

5. The process of claim 1, wherein the cation of the ionic liquid is selected from the group consisting of an N,N-dimethylethanolammonium ion, a triethanolammoniumion ion, and an N-butyldiethanolammonium ion.

6. The process of claim 1, wherein the anion of the ionic liquid is selected from the group consisting of bis(trifluoromethylsulphonyl)imide, formate, butanoate, pentanoate, hexanoate, heptanoate, octanoate, nonanoate, decanoate, glycolate, crotonate, pyruvate, succinate, and phenylacetate.

7. The process of claim 1, wherein the ionic liquid is selected from the group consisting of:

N-butyldiethanolammonium formate;
N-butyldiethanolammonium acetate;
N-butyldiethanolammonium propanoate;
N-butyldiethanolammonium butanoate;
N-butyldiethanolammonium pentanoate;
N-butyldiethanolammonium hexanoate;
N-butyldiethanolammonium heptanoate;
N-butyldiethanolammonium octanoate;
N-butyldiethanolammonium nonanoate;
N-butyldiethanolammonium decanoate;
N-butyldiethanolammonium benzoate;
N-butyldiethanolammonium benezenedicarboxylate;
N-butyldiethanolammonium benzenetricarboxylate;
N-butyldiethanolammonium benzenetetracarboxylate;
N-butyldiethanolammonium chlorobenzoate;
N-butyldiethanolammonium fluorobenzoate;
N-butyldiethanolammonium pentachlorobenzoate;
N-butyldiethanolammonium pentafluorobenzoate;
N-butyldiethanolammonium glycolate;
N-butyldiethanolammonium pantothenate;
N-butyldiethanolammonium mandelate;
N-butyldiethanolammonium crotonate;
N-butyldiethanolammonium malate;
N-butyldiethanolammonium pyruvate;
N-butyldiethanolammonium succinate;
N-butyldiethanolammonium citrate;
N-butyldiethanolammonium phenylacetate;
N-butyldiethanolammonium oxalate;
N-butyldiethanolammonium bis(trifluoromethylsulphonyl)imide;
N-butyldiethanolammonium carbonate;
N-butyldiethanolammonium hydrogen carbonate;
N-butyldiethanolammonium sulphate;
N-butyldiethanolammonium hydrogen sulphate;
N-butyldiethanolammonium methanesulphonate;
N-butyldiethanolammonium trifluoromethanesulphonate;
N-butyldiethanolammonium ethylenediaminetetraacetate;
N-butyldiethanolammonium hexafluorophosphate;
N-butyldiethanolammonium tetrafluoroborate;
N-butyldiethanolammonium trifluoroacetate;
N-butyldiethanolammonium pentafluoropropanoate;
N-butyldiethanolammonium heptafluorobutanoate;
N,N-dimethylethanolammonium formate;
N,N-dimethylethanolammonium acetate;
N,N-dimethylethanolammonium propanoate;
N,N-dimethylethanolammonium butanoate;
N,N-dimethylethanolammonium pentanoate;
N,N-dimethylethanolammonium hexanoate;
N,N-dimethylethanolammonium heptanoate;
N,N-dimethylethanolammonium octanoate;
N,N-dimethylethanolammonium nonanoate;
N,N-dimethylethanolammonium decanoate;
N,N-dimethylethanolammonium benzoate;
N,N-dimethylethanolammonium benezenedicarboxylate;
N,N-dimethylethanolammonium benzenetricarboxylate;
N,N-dimethylethanolammonium benzenetetracarboxylate;
N,N-dimethylethanolammonium chlorobenzoate;
N,N-dimethylethanolammonium fluorobenzoate;
N,N-dimethylethanolammonium pentachlorobenzoate;
N,N-dimethylethanolammonium pentafluorobenzoate;
N,N-dimethylethanolammonium glycolate;
N,N-dimethylethanolammonium pantothenate;
N,N-dimethylethanolammonium mandelate;
N,N-dimethylethanolammonium crotonate;
N,N-dimethylethanolammonium malate;
N,N-dimethylethanolammonium pyruvate;
N,N-dimethylethanolammonium succinate;
N,N-dimethylethanolammonium citrate;
N,N-dimethylethanolammonium phenylacetate;
N,N-dimethylethanolammonium oxalate;
N,N-dimethylethanolammonium bis(trifluoromethylsulphonyl)imide;
N,N-dimethylethanolammonium carbonate;
N,N-dimethylethanolammonium hydrogen carbonate;
N,N-dimethylethanolammonium sulphate;
N,N-dimethylethanolammonium hydrogen sulphate;
N,N-dimethylethanolammonium methanesulphonate;
N,N-dimethylethanolammonium trifluoromethanesulphonate;
N,N-dimethylethanolammonium ethylenediaminetetraacetate;
N,N-dimethylethanolammonium hexafluorophosphate;
N,N-dimethylethanolammonium tetrafluoroborate;
N,N-dimethylethanolammonium trifluoroacetate;
N,N-dimethylethanolammonium pentafluoropropanoate; and
N,N-dimethylethanolammonium heptafluorobutanoate.

* * * * *